United States Patent
Suriyapa

[11] Patent Number: 5,358,488
[45] Date of Patent: Oct. 25, 1994

[54] DEVICE TO CONTROL GASTROSTOMY LEAKAGE

[76] Inventor: Chinda Suriyapa, 6761 Gaines Mill Dr., Sylvania, Ohio 43560

[21] Appl. No.: 153,827

[22] Filed: Nov. 16, 1993

[51] Int. Cl.⁵ .......................................... A61M 29/00
[52] U.S. Cl. ........................................ 604/96; 604/178
[58] Field of Search ............................. 604/96–101, 604/174, 175, 178, 247

[56] References Cited

U.S. PATENT DOCUMENTS

| | | | |
|---|---|---|---|
| 4,069,826 | 1/1978 | Sessions et al. | 604/178 X |
| 4,089,337 | 5/1978 | Kronner | 604/178 X |
| 4,666,433 | 5/1987 | Parks | 604/178 |
| 4,685,901 | 8/1987 | Parks | 604/96 |
| 4,863,438 | 9/1989 | Gauderer et al. | 604/247 |
| 4,944,732 | 7/1990 | Russo | 604/247 |
| 5,061,240 | 10/1991 | Cherian | 604/96 |
| 5,112,310 | 5/1992 | Grobe | 604/175 |
| 5,125,897 | 6/1992 | Quinn et al. | 604/99 |

*Primary Examiner*—John D. Yasko
*Attorney, Agent, or Firm*—Emch, Schaffer, Schaub & Porcello Co.

[57] ABSTRACT

A gastrostomy device including an elongate feeding tube having a first end for insertion through an opening in a patient's abdominal wall and a second end including a feeding inlet. An inflatable balloon is mounted near the first end and a leakage seal valve is connected adjacent the balloon. The seal valve includes a flexible, elastomeric member to seal the opening in the patient and prevent leakage.

12 Claims, 2 Drawing Sheets

DEVICE TO CONTROL GASTROSTOMY LEAKAGE

BACKGROUND OF THE INVENTION

The present invention is directed to a gastrostomy device and more specifically to a gastrostomy tube assembly. While gastrostomy tube assemblies have been known in the past, a problem remains in the art in that leakage occurs around gastrostomy tubes in some patients. A typical use for a gastrostomy tube assembly is to feed patients in both hospital and nursing home settings.

Gastrostomy tube assemblies for long-term total or supplemental feeding have been widely used among the elderly population for several decades. The majority of patients who have such feeding tubes will not have any significant problems. However, certain groups of patients experience significant and persistent leakage around the tubes. The persistent leakage causes annoying skin maceration and patient discomfort. The use of inflatable balloons in connection with gastrostomy tubes is well known. However, even with balloon type gastrostomy tube assemblies, the persistent leakage still occurs. A typical prior art gastrostomy tube assembly is disclosed in U.S. Pat. No. 4,685,901 issued Aug. 11, 1987.

SUMMARY OF THE INVENTION

The present invention is directed to a gastrostomy device which includes an elongate feeding tube having a first end for insertion through a patient's abdominal wall and a second end. The second end is exterior of the patient's abdominal wall and includes a feeding inlet. An inflatable balloon is mounted on the feeding tube near the first end. A fluid supply conduit near the second end is in communication with the balloon. The balloon can be inflated upon correct positioning of the first end within the patient. A leakage seal valve is connected to the first end of the feeding tube adjacent the balloon. The leakage seal valve includes a flexible elastomeric member to seal the opening in the patient and prevent leakage upon inflation of the balloon.

Preferably a tube holding device is positioned exteriorly of the abdominal wall.

DESCRIPTION OF THE PREFERRED EMBODIMENTS

Figure 1:
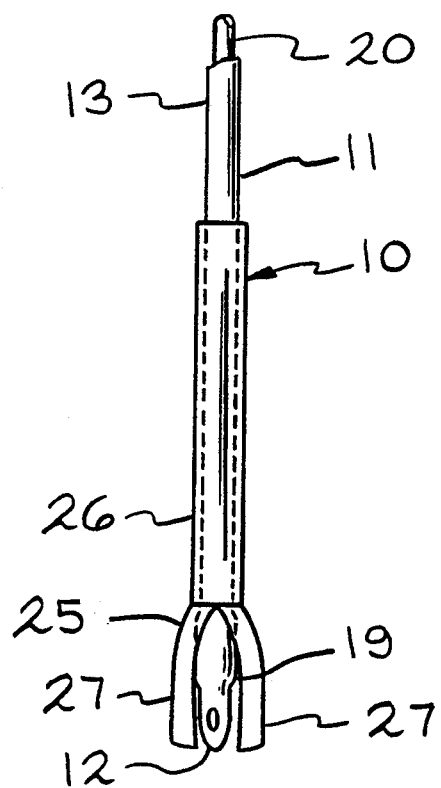
FIG. 1 is an elevational view of the gastrostomy device according to the present invention.
Figure 2:
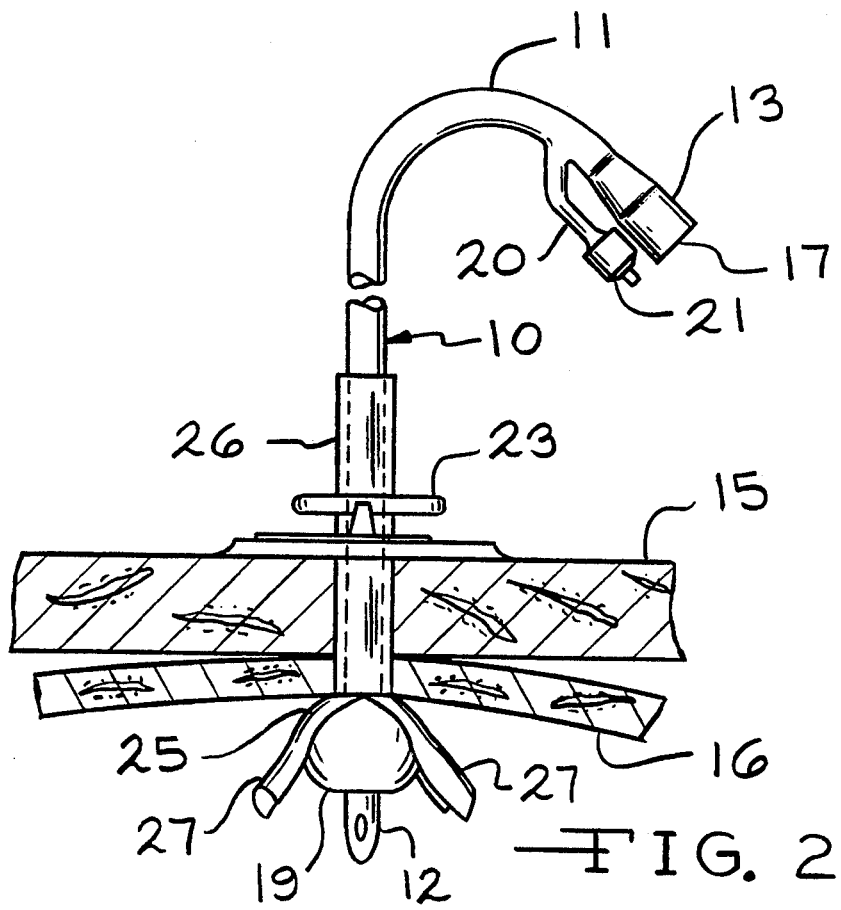
FIG. 2 is a view, partially in cross section, shoving the FIG. 1 embodiment installed in a patient.

A gastrostomy device, according to the present invention, is generally indicated by the reference number 10 in FIGS. 1 and 2. The gastrostomy device includes an elongate feeding tube 11 having a first end 12 and a second end 13.

Referring to FIG. 2, the first end 12 is inserted through an opening in the abdominal wall 15 and gastric wall 16 of the patient.

The second end 13 of the feeding tube 11 includes a feeding inlet 17. An integral inflatable balloon 19 is mounted on the feeding tube 11 near the first end 12. A fluid supply conduit 20 including a valve 21 is in communication with the balloon 19. As shown in FIG. 2, the balloon 19 is inflated upon correct positioning of the first end 12 of the feeding tube 11 within the patient. The fluid used to inflate the balloon 19 is normally air or water. A tube attachment device 23 holds the tube 11 in position against the exterior of the abdominal wall 15. The tube attachment device 23 is a prior art device such as one distributed by Hollister Incorporation.

An important feature of the present invention is a leakage seal valve 25 which is connected to the first end 12 of the feeding tube 11 adjacent the balloon 19, In the FIGS. 1 and 2 embodiment, the leakage seal valve 25 includes an elastomeric and flexible tubular member 26 which surrounds the first end 12 of the feeding tube 11. The seal valve 25 also includes two elastomeric sealing flaps 27.

When the first end 12 of the feeding tube 11 is correctly positioned and the balloon 19 inflated, the sealing flaps 27 seal the opening and prevents leakage through the abdominal wall 15.

The leakage experienced by most patients is intermittent, probably due to a transient increase in intragastric pressure. It has been found that when a gastrostomy device, according to the present invention is utilized, leakage does not occur around the gastrostomy feeding tube 11. The inventor believes that the intermittent increase in intragastric pressure pushes the valve sealing flaps 27 outward sealing the opening.

The feeding tube 11 and the leakage seal valve 25 are constructed of elastomeric materials such as latex materials or silicone elastomers.

Figure 3:
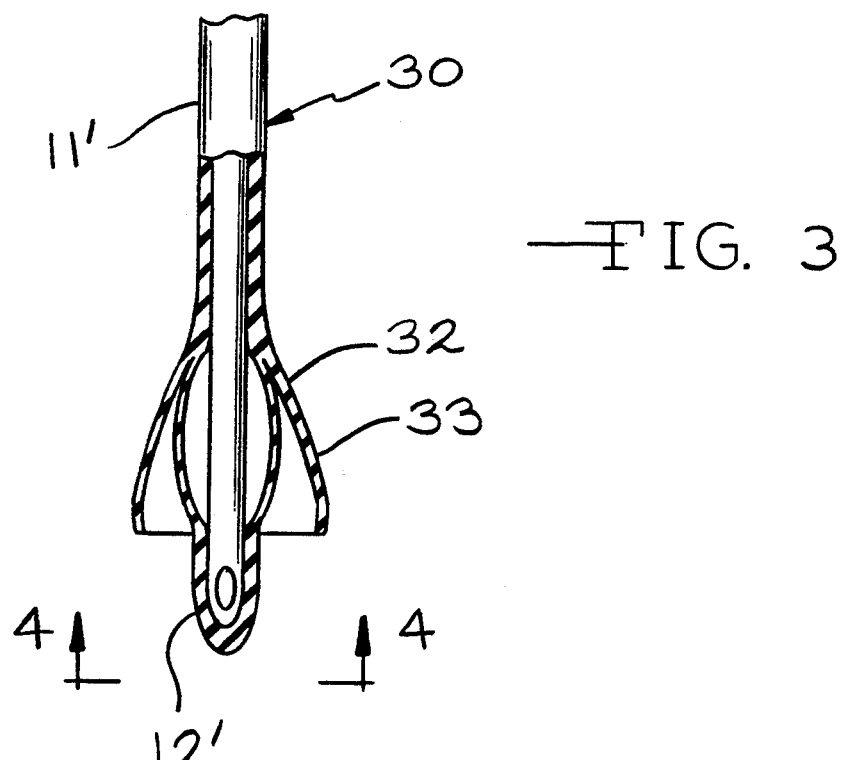
FIG. 3 is a sectional view of another embodiment of the gastrostomy device, according to the present invention.
Figure 4:
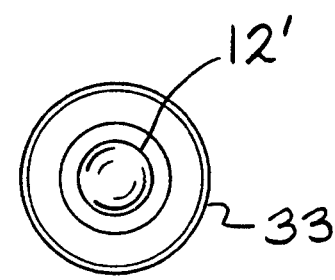
FIG. 4 is an end view taken along the line 4—4 of FIG. 3.
Figure 5:
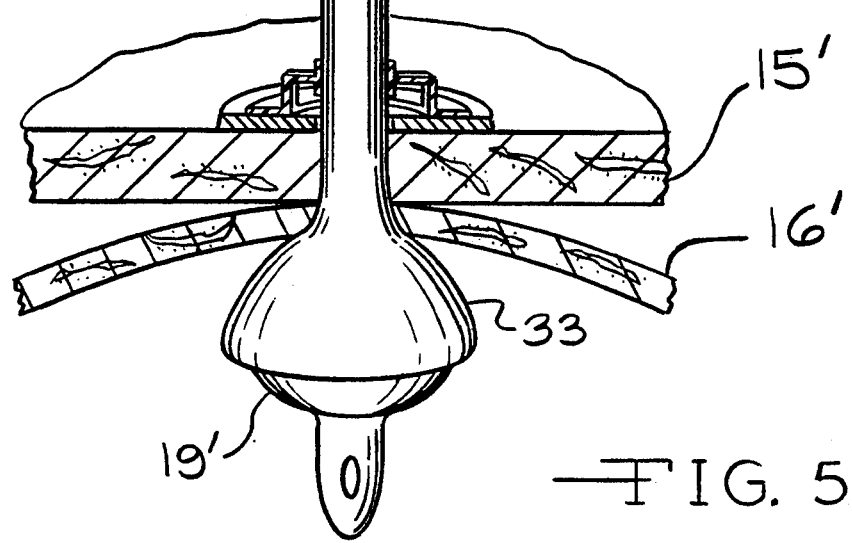
FIG. 5 is a partial perspective and partial sectional view showing the FIG. 3 embodiment installed in a patient.

Another embodiment of a gastrostomy device according to the present invention is shown in FIGS. 3-5 and indicated by the reference number 30. The gastrostomy device 30 is similar in construction to the device shown in FIGS. 1 and 2 with the exception of the construction of the leakage seal valve. In the gastrostomy device 30 a leakage seal valve 32 includes an integral elastomeric and continuous seal member 33 mounted on the first end 12' of the feeding tube 11' When the balloon 19' is inflated, the generally conically shaped flexible seal member 33 seals the patient opening to prevent leakage. The feeding tube 11' and the leakage seal valve 33 are constructed of elastomeric materials such as latex materials or silicone elastomers.

Many revisions may be made to the above described preferred embodiments without departing from the scope of the present invention or the following claims.

I claim:

1. A gastrostomy device comprising an elongated feeding tube having a first end for insertion through a patient's abdominal wall and a second end including a feeding inlet, an inflatable balloon mounted on said feeding tube near said first end, a fluid supply conduit near said second end in communication with said balloon, wherein said balloon can be inflated upon correct positioning of said first end within the patient and a leakage seal valve connected to said first end adjacent said balloon, said leakage seal valve including a flexible, elastomeric member mounted adjacent said balloon to seal the opening in the patient and prevent leakage upon inflation of said balloon.

2. A gastrostomy device, according to claim 1, wherein said leakage seal valve comprises an elastomeric generally conical seal member mounted on said first end adjacent said balloon.

3. A gastrostomy device, according to claim 1, wherein said leakage seal valve is integral with said feeding tube.

4. A gastrostomy device, according to claim 1, wherein said leakage seal valve is constructed of a latex material.

5. A gastrostomy device, according to claim 1, wherein said leakage seal valve is constructed of a silicone elastomer material.

6. A gastrostomy device, according to claim 1, including a tube attachment device positioned against the exterior of the abdominal wall of the patient.

7. A gastrostomy device comprising an elongated feeding tube having a first end for insertion through a patient's abdominal wall and a second end including a feeding inlet, an inflatable balloon mounted on said feeding tube near said first end, a fluid supply conduit near said second end in communication with said balloon, wherein said balloon can be inflated upon correct positioning of said first end within the patient and a leakage seal valve connected to said first end adjacent said balloon, said leakage seal valve including an elastomeric tubular member surrounding said feeding tube and two elastomeric sealing flaps extending from said tubular member adjacent said balloon, said sealing flaps sealing the opening in the patient upon inflation of said balloon.

8. A gastrostomy device comprising an elongated feeding tube having a first end for insertion through a patient's abdominal wall and a second end including a feeding inlet, an inflatable balloon mounted on said feeding tube near said first end, a fluid supply conduit near said second end in communication with said balloon, wherein said balloon can be inflated upon correct positioning of said first end within the patient and a leakage seal valve connected to said first end adjacent said balloon, said leakage seal valve comprising an elastomeric tubular member surrounding said feeding tube and at least two elastomeric sealing flaps adjacent said balloon.

9. A gastrostomy device, according to claim 8, wherein said leakage seal valve is integral with said feeding tube.

10. A gastrostomy device, according to claim 8, wherein said leakage seal valve is constructed of a latex material.

11. A gastrostomy device, according to claim 8, wherein said leakage seal valve is constructed of a silicone elastomer material.

12. A gastrostomy device, according to claim 8, including a tube attachment device positioned against the exterior of the abdominal wall of the patient.

* * * * *